(12) United States Patent
Hulteen, III

(10) Patent No.: US 7,174,847 B1
(45) Date of Patent: Feb. 13, 2007

(54) INSECT HABITAT AND FEEDER

(76) Inventor: William A. Hulteen, III, 5005 Sunbury Rd., Westerville, OH (US) 43082

(*) Notice: Subject to any disclaimer, the term of this patent is extended or adjusted under 35 U.S.C. 154(b) by 215 days.

(21) Appl. No.: 10/857,557

(22) Filed: May 28, 2004

Related U.S. Application Data

(60) Provisional application No. 60/320,228, filed on May 28, 2003.

(51) Int. Cl.
*A01K 29/00* (2006.01)
*A01K 1/03* (2006.01)
*A01K 97/00* (2006.01)

(52) U.S. Cl. .................. 119/6.5; 119/417; 119/427; 119/452; 43/55; 43/54.1; 43/132.1

(58) Field of Classification Search .............. 119/6.5, 119/6, 6.6, 417, 427, 454, 452, 472, 667, 119/669, 672, 453, 51.1; 43/54.1, 55, 132.1; 449/36, 39, 40
See application file for complete search history.

(56) References Cited

U.S. PATENT DOCUMENTS

| | | | | |
|---|---|---|---|---|
| 2,174,305 | A * | 9/1939 | Austin .................. | 119/6.5 |
| 2,718,088 | A * | 9/1955 | Perry et al. ............ | 43/55 |
| 2,745,209 | A * | 5/1956 | Kimball ................. | 43/55 |
| 2,843,968 | A * | 7/1958 | Dohrer .................. | 43/55 |
| 3,345,974 | A | 10/1967 | Phillips et al. | |
| 3,687,110 | A * | 8/1972 | Braunhut ............... | 119/6.5 |
| 3,999,519 | A | 12/1976 | Rodemeyer | |
| 4,207,993 | A | 6/1980 | Ellis, Sr. et al. | |
| 4,347,808 | A * | 9/1982 | Lester .................. | 119/51.04 |
| 4,585,112 | A * | 4/1986 | Peeling et al. .......... | 194/293 |
| 4,825,577 | A * | 5/1989 | Brannon ................ | 43/55 |
| 4,924,810 | A * | 5/1990 | Tominaga .............. | 119/6.5 |
| 5,133,290 | A * | 7/1992 | De Marco et al. ....... | 119/497 |
| 5,377,445 | A * | 1/1995 | Brannon ................ | 43/55 |
| 5,398,642 | A | 3/1995 | Harwich | |
| 5,630,374 | A | 5/1997 | Cunningham | |
| 6,561,125 | B1 | 5/2003 | Lohsomboon | |
| 6,877,269 | B2 * | 4/2005 | Schultz ................. | 43/55 |

FOREIGN PATENT DOCUMENTS

JP        06197667 A  *  7/1994

OTHER PUBLICATIONS

Kricket Keeper product information from website http://www.reptiledirect.com.
Cricket Corral product information from website http://www.pet-tech.com.

* cited by examiner

*Primary Examiner*—Peter M. Poon
*Assistant Examiner*—Andrea M. Valenti
(74) *Attorney, Agent, or Firm*—Standley Law Group LLP

(57) ABSTRACT

An insect storage, maintenance, dusting, and distribution device that dispenses living insects to caged animals. A Tower compartment is connected to a separate Dusting Chamber compartment with apertures on both compartments that may be aligned by rotating the Tower above the Dusting Chamber to form a passage for insects. The insects can move from the Tower to the Dusting Chamber which coats the insects with a nutritional dust. The insects are then allowed to move from the Dusting Chamber through a Feeder Tube into the animal(s)' habitat for their consumption by the animal.

15 Claims, 3 Drawing Sheets

INSECT HABITAT AND FEEDER

The present application incorporates by reference and claims the benefit of priority of presently pending U.S. Provisional Patent Application No. 60/320,228 filed on May 28, 2003.

BACKGROUND AND SUMMARY OF THE INVENTION

The present invention relates to a device for providing an insect habitat and feeder. More specifically, the present invention may be used to provide a convenient apparatus for the storage, dusting, and feeding of crickets to cricket-eating pets such as a reptile.

As described by Cunningham in U.S. Pat. No. 5,630,374, "Feeding crickets to one's pet reptile is an often messy and wasteful task. The crickets are generally packaged and brought from the store in plastic bags or cups. The pet owner will keep them in a lidded container, opening the container periodically to feed his pet. Each time, he must attempt to pour the correct number of crickets into the reptile's aquarium or other habitat as "excess" crickets are otherwise wasted due to their inability to seek food. Crickets often jump out of the container and escape into the house despite the owner's most careful efforts in doling out a meal. This forces customers to restrict their purchases to a two or three-day supply requiring frequent trips to the pet store."

The present invention provides a device that minimizes the need for the handling or pouring of crickets that, often times, provides the opportunity for their unintended escape. The present invention provides a device that lessens the requirement or the potential need to touch the crickets once they are loaded into the device. The present invention eliminates the need to pour or transfer crickets between storage and preparation containers. In addition, the present invention provides the ability to control the number of crickets prepared and released for feeding to the cricket-eating pet.

The present invention is a device that may be comprised of a first compartment, or a storage compartment—also called a Tower, that is connected to a second compartment, also called a Dusting Chamber. The connection between the Tower and the Dusting Chamber may be a pivot, a slidable engagement of surfaces, or rotationally connected along an axis. Each compartment has an aperture arranged so that the respective apertures of the compartments can be oriented so that at least a portion of both apertures align to provide a sufficiently sized passage for an insect, such as a cricket, to move between the compartments. This scenario places the device of the present invention in an open condition. Once the desired number of crickets has entered the Dusting Chamber, the device is placed in a closed condition by changing the relative orientation between the Tower and the Dusting Chamber. The device may be shaken so as to coat at least a portion of the crickets in the Dusting Chamber with a nutritional dust that is used to supplement the food supply and meet the nutritional needs of the cricket-eating pet. Typically, the entire device is placed into the cage with the cricket-eating pet. Then a feeder tube may be extended from the Dusting Chamber so that the crickets can crawl out of the device and be consumed by the pet. When all of the dusted crickets have crawled out of the Dusting Chamber, the device may be removed to be used at the next feeding.

Additional features of alternative embodiments of the device of the present invention may include receptacles for holding food and/or water for the crickets contained in the Tower portion. Another option provides a debris shield surrounding at least a portion of a perimeter of an aperture in either the first compartment or the second compartment. The debris shield may comprise a raised portion that prevents the transport of insect droppings, food, or other debris from falling through the passage and into another compartment while a device of the present invention is in an open condition. Another option provides a translucent or a visually obscuring shield that discourages or prevents a pet from pecking or biting the device of the present invention caused by seeing the crickets contained in the device. Another option of the present invention provides a substrate comprised of a leafy material or vines that makes for a suitable environment with climbing surfaces and hiding places for the crickets contained in the device. In addition, the present invention may have removable lids to facilitate the introduction of crickets, food, water, or nutritional dust to a compartment and/or for cleaning of the device.

An alternative embodiment of the present invention uses the vertical space in the Tower compartment with a climbing substrate. If crickets are confined to a small space and must constantly crawl over each other, they will begin destroying each other. To keep the device small and manageable and provide a small footprint for this embodiment of the present invention, the use of a climbing substrate and vertical space is preferred for this embodiment of the Tower.

An embodiment of the feeder tube of the present invention is placed through a complementary sized opening in the Dusting Chamber. It is preferred that the feeder tube should be sufficiently sized to provide an outlet from the Dusting Chamber for at least one insect to leave the device of the present invention through an exit hole. An alternative embodiment of the feeder tube is slidably connected to the complementary sized opening in the Dusting Chamber. In this embodiment, the feeder tube can be retracted or extended from the Dusting Chamber as needed to allow the release of insects from the device. An alternative embodiment of the feeder tube of the present invention provides for an egress for crickets from the device that potentially lessens the likelihood of damage to a cricket-eating pet. For example, once a reptile becomes accustomed to the location where the crickets exit the device, the reptiles will attempt to peck inside the device and potentially damage their skin on the edges or ridges of the exit hole. By orienting the exit hole of the feeder tube downward, the feeder tube allows the crickets to exit the device and minimizing the risk to the reptile.

An alternative embodiment of a feeder tube of the present invention is comprised of a tube; a closed end approximately on an end of the tube; a tube stop approximately on an end of the tube that is opposite the closed end; and an exit hole located on a portion of the longitudinal length of the tube. In this embodiment, the tube stop is attached to the tube so that the tube stop is prevented or discouraged (by requiring use of excessive force) from passage through the complementary sized opening in the Dusting Chamber, thusly resulting in separation of the feeder tube from the device. In addition, the closed end of the feeder tube, when retracted into the Dusting Chamber, provides a closed compartment that discourages an undesired loss of nutritional dust when the crickets contained therein are being coated prior to a feeding event.

As described above, the device of the present condition is in an open condition when at least a portion of the apertures between the compartments are aligned to provide sufficient space for a passage of an insect between the compartments. Conversely, the device is in a closed position when the apertures are unaligned. The unaligned apertures do not provide a passage sufficiently sized for an insect to move between the compartments. Alternative embodiments of the present invention may include a visual indicator of the device being in an open or closed condition. Such an indicator may be a simple alignment of arrows, pointers, or some other marker on the respective first and second compartments. An alignment of the marks may indicate an open condition. An alignment of the marks may indicate a closed condition. Moreover, the same device may have a set of marks to indicate an open condition and a separate set of marks to indicate a closed condition. In addition, an alternative embodiment of the present invention provides for the exterior shape of at least one of the compartments to be visually distinguishable between an open condition and a closed condition for the device of the present invention. For example, a compartment may be rectangular so that when a device is in an open condition, the longer side of the rectangle may be oriented in a particular direction. Alternatively, both compartments of an embodiment of the present invention may combine to make a complementary shape that gives a clear visual indicator of a device in an open or a closed condition. The shapes may be geometric or comprised of three dimensional shapes such as a cricket or a reptile.

Alternative embodiments of the present invention may provide a rotational stop, wherein the rotational stop limits the rotational position of the first compartment relative to the second compartment. For example, a full quarter turn of one compartment to the right relative to another compartment up to a rotational stop may be predetermined to place a device in an open condition. Alternatively, a full half turn to the left up to a rotational stop could place another device in a closed condition.

Alternative embodiments of the present invention may include at least one vent in at least one of the compartments for the ventilation of a portion of the device. These vents may be a series of small holes that provide for the movement of air through the device, while preventing the unintended release of the insects from the compartments of the device.

Alternative embodiments of the present invention may be comprised of a material suitable for the storage of insects such as crickets. A preferred material is comprised of plastic. Portions of a preferred material may be clear or opaque, however it is preferred that at least a portion of the material allows for a visual inspection of the Dusting Chamber so that a user will know how many insects are being prepared for release during a feeding event.

BRIEF DESCRIPTION OF THE DRAWINGS

In addition to the novel features and advantages mentioned above, other objects and advantages of the present invention will be readily apparent from the following descriptions of the drawings and preferred embodiments.

DETAILED DESCRIPTION OF THE
EXEMPLARY EMBODIMENT(S)

The exemplary embodiments discussed below are preferably made from a plastic material. Preferred embodiments of at least portions of the present invention may be manufactured via an injection molded plastic process. In addition to plastic, at least portions of the present invention may be made from other similar material including plastic-containing compounds. At least portions of the present invention may be manufactured from metals, such as aluminum, steel, or stainless steel. Other suitable materials for use in the manufacture of alternative embodiments include those materials well known in the art for animal care and feeding.

Figure 1:
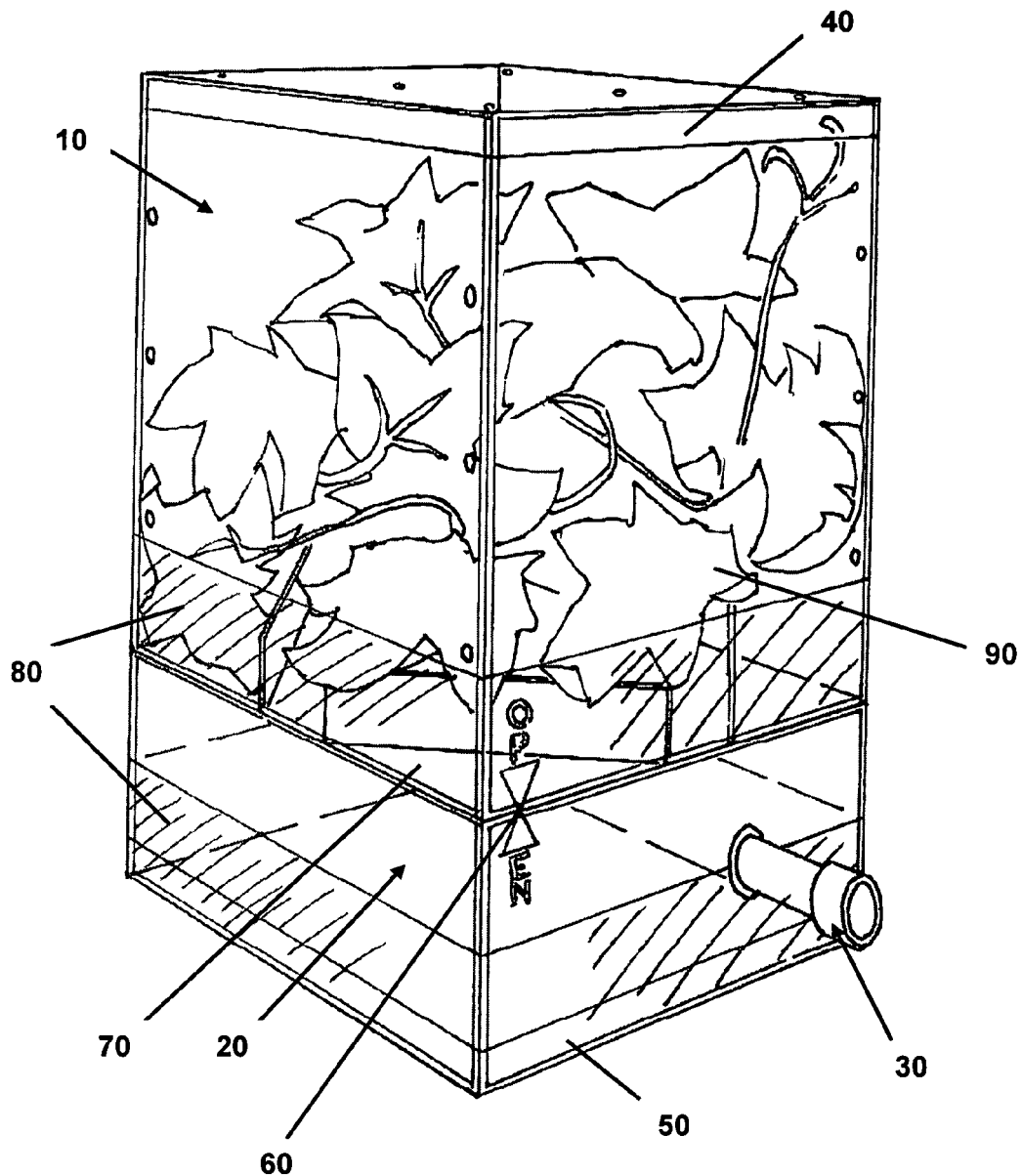
FIG. 1 is a perspective view of an embodiment of the present invention.

An exemplary embodiment of a device of the present invention is shown in a perspective view at FIG. 1. A first compartment 10 is shown above a second compartment 20. The first compartment 10 and second compartment 20 are also known as a Tower and a Dusting Chamber, respectively. A feeder tube 30 is shown entering the second compartment through a complementary sized opening. As shown below, the feeder tube 30 may be slidably connected to the second compartment 20 at the complementary sized opening. In addition, FIG. 1 shows a removable lid 40 and a removable lid 50 that provide access to the first compartment 10 and the second compartment 20, respectively. The removal of a lid 40 or 50 may facilitate the addition of crickets or some other insect, food, water, or nutritional dust into a compartment. In addition, the removal of the lids may facilitate cleaning the compartments 20 and 30.

FIG. 1 also shows a visual indicator and rotational stop at 60. In this embodiment of the present invention, the visual indicator shows the device in an open condition. As described below, the open condition is a state whereby a passage is formed between the first compartment 10 and the second compartment 20 by an alignment of at least a portion of each compartments' respective apertures. The open condition need only indicate that the passage is sufficiently sized to allow an insect to move between the first compartment 10 and the second compartment 20. The open condition does not have to necessarily indicate a precise alignment of the apertures. In this manner, a user of the device of the present invention can partially control the movement of insects between compartments by varying or throttling the size of the passage between the compartments. In addition, the visual indicator and rotational stop 60 may prevent the rotational displacement of the first container 10 relative to the second container 20 by hindering the relative movement between the compartments with a physical stop such as the tip of the arrow shown at 60.

FIG. 1 also shows a receptacle 70 inside the first compartment 10. This receptacle may be used as a holder for food or water for the insects living inside the first compartment. This example embodiment shows the receptacle can be easily inspected by a user of the device. In addition, a translucent shield 80 obscures the view of the bottom portions of the first compartment 10 and the second compartment 20. As discussed previously, the obscured view into the compartments 10 and 20 discourages the insect-eating animal from attempting to eat insects that are safely contained inside a compartment, thus preventing a potential injury to an overzealous animal that may continue to attempt to capture the unobtainable insects contained therein. Another option of the present invention provides a substrate 90 comprised of a leafy material or vines that makes for a suitable environment with climbing surfaces and hiding places for the crickets contained in the device.

Figure 2:
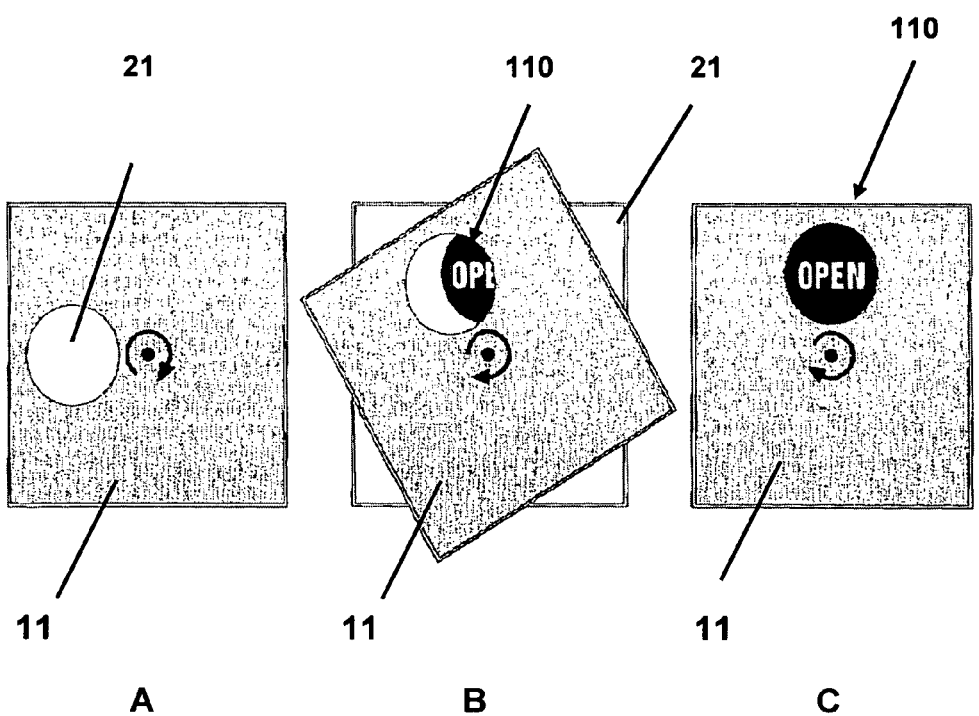
FIG. 2 is a top elevational view of a series of figures showing the rotational alignment of apertures of the compartments of an embodiment of the present invention.

FIG. 2 is a top elevational view of a series of figures showing the rotational alignment of apertures of the compartments of an embodiment of the present invention. As shown at A, B, and C on FIG. 2, a portion of a first compartment having an aperture 11 is shown positioned over a portion of a second compartment having an aperture 21. A shows the apertures unaligned in what is called a closed condition for an example embodiment of the present invention. B shows the portion of a first compartment having an aperture 11 being rotated in a clockwise direction relative to the portion of a second compartment having an aperture 21. As can been seen at B, the aperture of the second compartment having an aperture 21 is coming into view through the aperture of the first compartment having an aperture 11. Finally at C, the apertures are aligned, thus providing a sufficiently sized passage 110 between the first compartment and the second compartment to allow the movement of an insect between the compartments.

Figure 3:
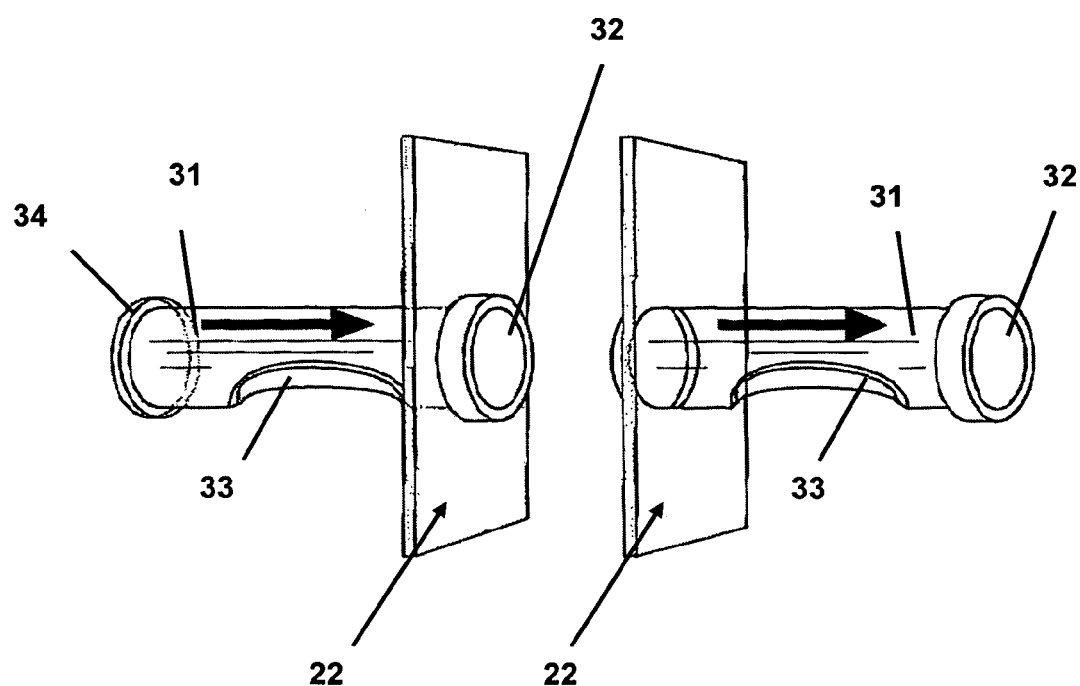
FIG. 3 is a perspective view of a series of figures showing an embodiment of the feeder tube of the present invention.

FIG. 3 is a perspective view of a series of figures showing an embodiment of the feeder tube of the present invention. A tube 31 is shown passing through a portion of the second compartment 22 through a complementary sized opening. The fit between the outer diameter of the tube 31 and the complementary sized opening of the second compartment 22 provides a slidable connection between those elements. In addition, a tube stop 34 is shown having a slightly larger diameter than the tube 31. As the tube 31 is slid out of the second compartment, the tube 31 is prevented from an unintended removal from the device as the tube stop 34 will not pass easily though the complementary sized opening. Although the tube stop 34 is depicted as a ring slightly larger than the outer diameter of the tube 31, other tube stops may be as simple as a post projecting from the side of a tube. Another alternative for a tube stop may be described as a gradual swaging of at least the outer diameter of a tube so that additional extraction of the tube is discouraged.

FIG. 3 also shows a closed end 32 on an end of the tube 31 opposite the tube stop 34. When the tube 31 is retracted into the second compartment, the closed end 32 effectively closes the outlet of the device of the present invention by placing the exit hole 33 inside of the second compartment. As can be seen in FIG. 3, when the tube 31 is extracted from the second compartment, the exit hole 33 provides an egress for insects from the second compartment.

The preferred embodiments herein disclosed are not intended to be exhaustive or to unnecessarily limit the scope of the invention. The preferred embodiments were chosen and described in order to explain the principles of the present invention so that others skilled in the art may practice the invention. Having shown and described preferred embodiments of the present invention, those skilled in the art will realize that many variations and modifications may be made to affect the described invention. Many of those variations and modifications will provide the same result and fall within the spirit of the claimed invention. It is the intention, therefore, to limit the invention only as indicated by the scope of the claims.

I claim:

1. A device providing an insect habitat and feeder, the device comprising:
    a first compartment having a first aperture in a first surface thereof;
    a second compartment having a second aperture in a first surface thereof, the second compartment connected to the first compartment with the respective first surfaces in facing relationship; and
    a tube positioned for sliding axial movement in a third aperture in a second surface of the the second compartment, the tube having a first open end and a closed second end with an intermediate portion therebetween, the tube having an enlarged outer diameter at each end to limit the axial movement and a radial opening along the intermediate portion near the second end, the tube providing a passage from the second compartment to an exterior of the device;
    wherein aligning at least a portion of the first and second apertures sufficiently to allow an insect in one of the compartments to move to the other compartment defines an open condition of the device and moving the respective apertures out of alignment so that an insect is unable to move from one of the compartments to the other defines a closed condition of the device.

2. The device of claim 1, wherein the first compartment is rotationally connected to the second compartment along an axis.

3. The device of claim 2, said device additionally comprising a rotational stop, wherein said rotational stop limits the rotational position of said first compartment relative to said second compartment.

4. The device of claim 1, wherein the first and second compartments comprise a plastic.

5. The device of claim 1, further comprising: a removable lid providing access to the first compartment.

6. The device of claim 1, further comprising: a removable lid providing access to the second compartment.

7. The device of claim 1, further comprising: a visual indicator that the device is in an open condition.

8. The device of claim 1, further comprising: a visual indicator that the device is in a closed position.

9. The device of claim 1, further comprising:
    at least one vent in at least one of said compartments.

10. The device of claim 1, further comprising:
    at least one receptacle inside the first compartment, providing a holder for food or water for insects contained in the first compartment.

11. The device of claim 1, wherein at least one of the compartments is comprised of a shield that visually obscures at least a portion of the compartment.

12. The device of claim 11, wherein said shield is translucent.

13. The device of claim 1, further comprising: a substrate inside at least one of said compartments providing an environment for insects.

14. The device of claim 13, wherein said substrate provides an environment for insects to climb and hide.

15. The device of claim 1, wherein the tube is comprised of a plastic material.

* * * * *